United States Patent
Richey, II et al.

(10) Patent No.: US 6,302,107 B1
(45) Date of Patent: *Oct. 16, 2001

(54) APPARATUS AND METHOD FOR FORMING OXYGEN-ENRICHED GAS AND COMPRESSION THEREOF FOR HIGH-PRESSURE MOBILE STORAGE UTILIZATION

(75) Inventors: Joseph B. Richey, II, Chagrin Falls; Gerold G. Goertzen, Brunswick, both of OH (US)

(73) Assignee: Invacare Corporation, Elyria, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/154,442

(22) Filed: Sep. 16, 1998

Related U.S. Application Data

(63) Continuation-in-part of application No. 08/942,063, filed on Oct. 1, 1997, now Pat. No. 5,988,165.

(51) Int. Cl.$^7$ ................................. A62B 7/00; A62B 9/00
(52) U.S. Cl. ................................. 128/205.18; 128/205.11; 95/96
(58) Field of Search ................. 128/200.24, 204.18, 128/204.21, 204.22, 204.26, 204.24, 204.25, 205.11, 205.12, 205.18; 95/8, 96, 121, 130; 96/111, 130, 144; 92/73, 179, 240; 417/254, 256, 415, 522

(56) References Cited

U.S. PATENT DOCUMENTS

| | | |
|---|---|---|
| 519,423 | 4/1993 | Harral et al. . |
| 2,944,627 | 7/1960 | Skarstrom . |
| 3,313,091 | 4/1967 | Berlin . |
| 3,898,047 | 8/1975 | Cramer . |
| 4,013,429 * | 3/1977 | Sircar et al. .............................. 55/33 |
| 4,194,890 | 3/1980 | McCombs et al. . |
| 4,222,750 | 9/1980 | Gauthier et al. . |
| 4,331,455 | 5/1982 | Sato . |
| 4,428,372 | 1/1984 | Beysel et al. . |
| 4,449,990 | 5/1984 | Tedford, Jr. . |
| 4,552,571 * | 11/1985 | Dechene .................................. 55/21 |
| 4,627,860 | 12/1986 | Rowland . |

(List continued on next page.)

FOREIGN PATENT DOCUMENTS

| | | |
|---|---|---|
| 0 860 647 | 8/1998 | (EP) . |
| 374 540 | 6/1932 | (GB) . |

*Primary Examiner*—John G. Weiss
*Assistant Examiner*—Joseph F. Weiss, Jr.
(74) *Attorney, Agent, or Firm*—Hudak & Shunk Co., L.P.A.

(57) ABSTRACT

An oxygen concentrator is utilized in combination with a compressor to provide a highly enriched and compressed oxygen gas in a mobile container such as a gas cylinder. The combination and method of production provides for the facile preparation of an enriched source of oxygen for use by an ambulatory or wheelchair-confined patient. The oxygen concentrator utilizes two or more molecular sieves to provide a breathable gas of from approximately 80 to about 98 percent oxygen from atmospheric air. The oxygen-enriched gas is stored in a concentrator product tank and can be prioritized so as to supply a patient with a proper amount and concentration of oxygen and secondarily to supply any surplus or excess enriched oxygen to a compressor. The compressor utilizes multiple stages to produce the highly compressed oxygen-enriched gas and utilizes a two-part piston at low rpm to enhance low wear and low noise. The multiple pistons of the compressor can either all rotate at one RPM or in an alternative embodiment, at least a first piston can rotate at a higher RPM than any remaining pistons. Desirably, at least the initial piston of the alternative embodiment is driven by one drive shaft source with one or more other remaining pistons being driven by a second drive shaft.

22 Claims, 10 Drawing Sheets

U.S. PATENT DOCUMENTS

| | | |
|---|---|---|
| 4,636,226 | 1/1987 | Canfora . |
| 4,673,415 * | 6/1987 | Stanford ................... 55/21 |
| 4,706,664 | 11/1987 | Snook et al. . |
| 4,765,804 * | 8/1988 | Lloyd-Williams et al. ............ 55/16 |
| 4,844,059 | 7/1989 | Koch . |
| 4,867,766 * | 9/1989 | Campbell ............................... 55/161 |
| 4,869,733 * | 9/1989 | Stanford ................... 55/21 |
| 4,905,685 | 3/1990 | Olsson et al. . |
| 4,922,900 * | 5/1990 | Kiske et al. .................... 128/202.27 |
| 4,991,616 | 2/1991 | Fabregat . |
| 5,071,453 * | 12/1991 | Hradek et al. ............................ 55/21 |
| 5,144,945 | 9/1992 | Nishino et al. . |
| 5,163,978 * | 11/1992 | Leavitt et al. ............................ 55/18 |
| 5,195,874 | 3/1993 | Odagiri . |
| 5,199,423 | 4/1993 | Harral et al. . |
| 5,207,806 * | 5/1993 | Lagree et al. ............................ 55/16 |
| 5,237,987 | 8/1993 | Anderson et al. . |
| 5,354,361 * | 10/1994 | Coffield ................... 95/103 |
| 5,405,249 * | 4/1995 | Benson ................... 417/313 |
| 5,474,595 | 12/1995 | McCombs . |
| 5,584,669 | 12/1996 | Becker . |
| 5,593,291 * | 1/1997 | Lynn ................... 417/539 |
| 5,593,478 * | 1/1997 | Hill et al. ............................... 96/111 |
| 5,704,964 * | 1/1998 | Kaneko et al. .......................... 95/23 |
| 5,730,778 * | 3/1998 | Hill et al. ................... 95/12 |
| 5,858,062 * | 1/1999 | McCulloh et al. ........................ 95/8 |
| 5,893,944 * | 4/1999 | Dong et al. ............................ 96/114 |
| 5,988,165 * | 11/1999 | Richey, II et al. ............. 128/205.12 |

* cited by examiner

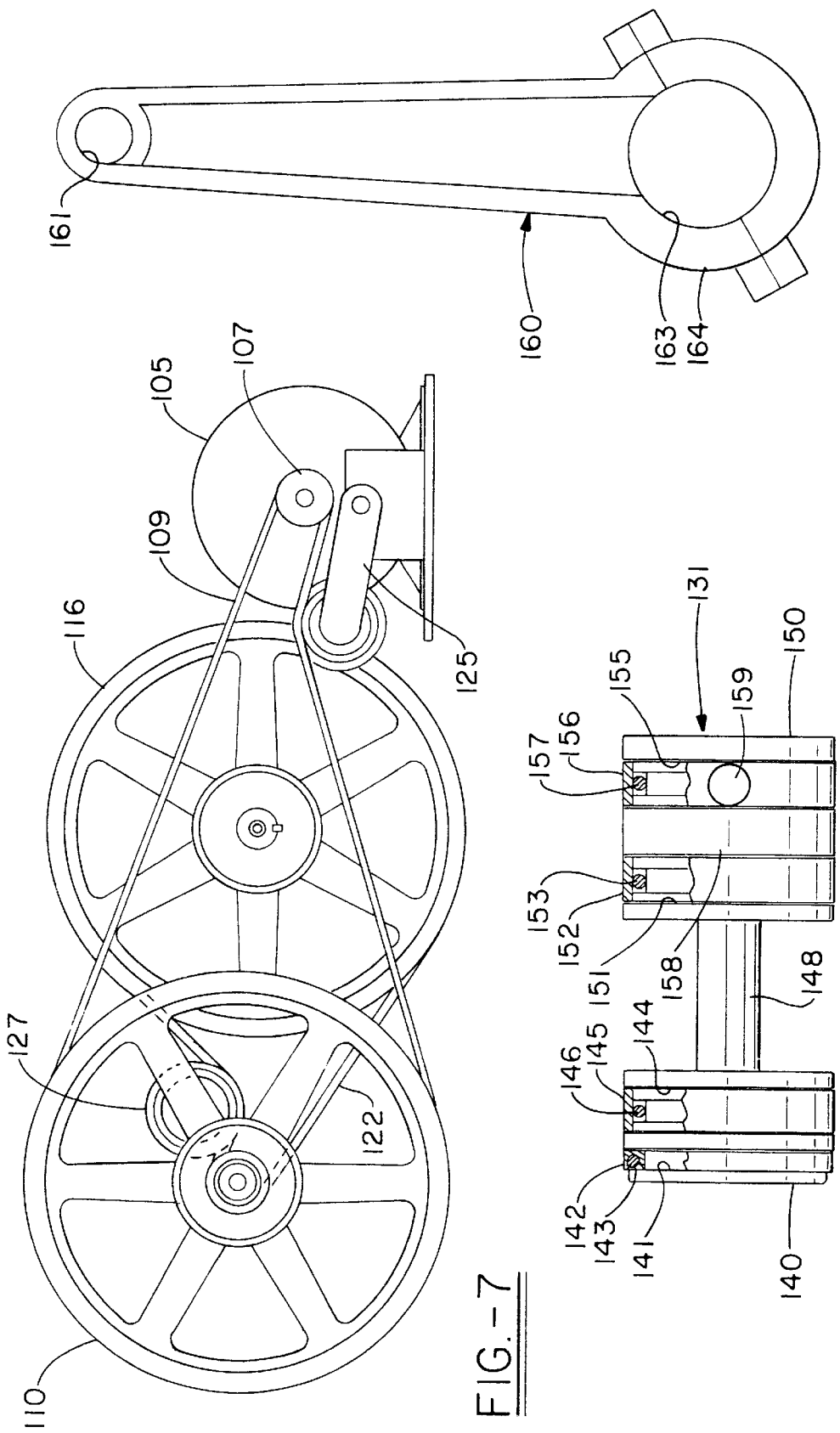

APPARATUS AND METHOD FOR FORMING OXYGEN-ENRICHED GAS AND COMPRESSION THEREOF FOR HIGH-PRESSURE MOBILE STORAGE UTILIZATION

CROSS-REFERENCE

This application is a continuation-in-part of U.S. Ser. No. 08/942,063, filed Oct. 1, 1997 for an Apparatus and Method for Forming Oxygen-Enriched Gas and Compression Thereof for High Pressure Mobile Storage Utilization now U.S. Pat. No. 5,988,165."

FIELD OF INVENTION

The present invention relates to an apparatus and process for producing enriched oxygen which is subsequently collected under high pressure in a portable container for ambulatory patient use and to permit facile patient mobility. A compressor can have all the pistons thereof operated by a single drive shaft, or an alternative, compact compressor can utilize at least two different drive shafts having at least one piston reciprocating at a higher RPM than one or more of the remaining pistons.

BACKGROUND OF THE INVENTION

Heretofore, oxygen concentrators have been utilized to supply patients with a gas having a high oxygen concentration for extended periods of time. Oxygen concentrators typically produce a breathable gas containing from about 80 present to about 96 present oxygen from atmospheric air and thus have been widely utilized in the home health care field.

U.S. Pat. No. 4,627,860, to Rowland, relates to a microprocessor and cooperating means for monitoring or sensing functions and performance of various components of the concentrator. A test apparatus having means for selecting any of the functions monitored by the microprocessor is connected to the concentrator and displays the selected monitored functions for diagnosing performance levels and component problems or failures.

U.S. Pat. No. 5,071,453, to Hiradek et al. relates to an oxygen concentrator which is intended for aircraft use. A booster compressor is used to increase the pressure of the product gas from the concentrator in order to increase the amount of the gas which can be stored in a plenum. The booster includes two moving pistons which are rigidly linked together and a series of check valves which control the flow of gases through the compressor. One of the pistons is driven by air from the rotary valve in the concentrator, and the other piston compresses the product gas for delivery to the plenum. A small sample of concentrator product gas is monitored by an oxygen sensor for oxygen concentration. Once the oxygen concentration has reached an acceptable level, the booster compressor fills the plenum with product gas. Thereafter, if the oxygen concentration of product gas delivered to the crew from the concentrator falls below the concentration which is required at a particular altitude, the product gas stored in the plenum is delivered to the crew. The oxygen sensor monitors the concentrator output product gas to the breathing regulator when the stored plenum gas is not being used.

U.S. Pat. No. 5,354,361, to Coffield, relates to a pressure-swing adsorber system including a pneumatically driven booster compressor to increase the pressure of the output product gas. A pair of inlet valves controls feed air flow to the sieve beds and the drive cylinder of the booster compressor and are cycled so that one valve opens to pressurize one sieve bed before the other valve closes to allow the other sieve bed to vent to atmosphere. During the time that both valves are open, the pressure in the two sieve beds and on opposite sides of the drive cylinder equalize and a portion of the gas in the pressurized sieve bed and drive cylinder side is captured rather than being vented to ambient. System efficiency is increased by selecting whether captured gas from the last pressurized sieve bed or drive cylinder side reaches the next to be pressurized sieve bed first.

SUMMARY OF THE INVENTION

It is an aspect of the present invention to provide a method and apparatus for storing high-pressure, high-purity oxygen in a pressure vessel for use in the home health care or related fields as for ambulatory patients, persons confined to wheelchairs, and those who are bedridden.

In accordance with the invention there is provided a method and apparatus for producing from air an oxygen-enriched gas and initially storing the same in a concentrator product tank. Desirably but secondarily, at least a portion of the oxygen-enriched gas is fed by different methods to a compressor buffer tank where it is stored. After reaching a predetermined pressure, the gas is fed to a compressor where it is compressed to a high pressure and stored in a mobile or portable high-pressure container. This eliminates the requirement of an oxygen concentrator which contains a first compressor and requires connection to an electrical outlet. A patient can thus have increased mobility through use of the portable, high-pressure oxygen container.

It is a further aspect of the invention to provide electrical circuitry to assure prioritization of the flow rate and concentration of the enriched gas to a patient.

The excess gas, when available, is simultaneously delivered to an independent, multi-stage compressor.

In accordance with another aspect of the invention there is provided a home health care oxygen concentrator for physically separating molecules of oxygen from air with oxygen in a subsequent operation being fed to a high-pressure vessel. The concentrator comprises one or more molecular sieve beds containing a physical separation material, a first (i.e., feed stock) compressor to provide a feed source of compressed air, control means which regulate the product gas flow through the beds to a concentrator product tank, a second enriched-gas storage tank (i.e., a buffer tank), and a second compressor, e.g., multi-stage, which is not operated by the first compressor but operates independently thereof and enables the oxygen-enriched gas to be compressed and fed to a high-pressure vessel or container. The second compressor has a two-part piston assembly which results in low wear. In an alternative embodiment, a compressor can be utilized which has a variety of features such as a first stage wobble piston connected to a first drive shaft, one or more subsequent pistons sequentially aligned to increase the pressure of a gas with such pistons being connected to a second drive shaft, and a bleed-off valve which serves to abate noise when the compressor is disconnected from the high pressure vessel. The alternative compressor is compact, lightweight, and cost efficient.

BRIEF DESCRIPTION OF THE DRAWINGS

FIG. 7 is a side elevational view of the compression apparatus of the present invention;

FIG. 9 is a side elevational view of the upper portion of the two-part piston assembly of the present invention;

FIG. 10 is a side elevational view of the bottom portion of the two-part piston assembly of the present invention.

DETAILED DESCRIPTION OF THE PREFERRED EMBODIMENT

While a preferred embodiment of the invention is described hereinbelow, it is to be understood that the various aspects and parameters of the present invention can vary and be different such as the pressure and purity of the oxygen-enriched gas exiting from a concentration product tank, the pressure at which the enriched gas is fed to the patient and its flow rate, the pressure maintained in a buffer tank, the pressure at which the compressor initially draws enriched gas from the buffer tank, the buffer tank pressure at which the compressor shuts off, and the like. Moreover, while reference is made to a particular oxygen concentrator as set forth immediately below, generally any type of oxygen concentrator can be utilized which yields a source of enriched air containing anywhere from about 50 percent oxygen up to about 99 percent by volume.

Figure 1:
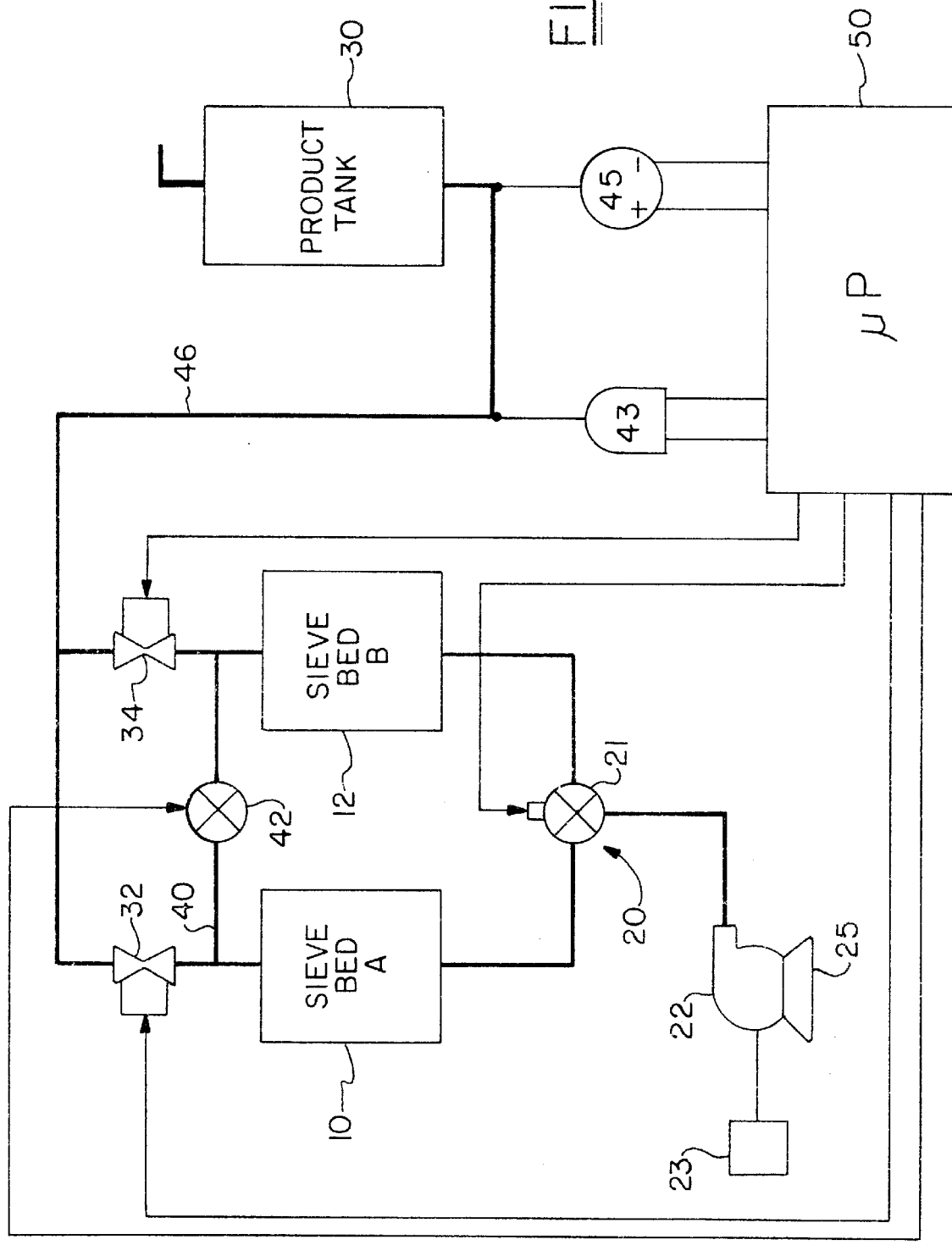
FIG. 1 is a block diagram of an oxygen concentrator for separating oxygen from a gaseous mixture such as air.

With reference to FIG. 1, the apparatus includes one or more, and preferably two beds 10 and 12 which contain a physical separation medium or material. The separation material selectively adsorbs one or more adsorbable components as from air and passes one or more nonadsorbable components of such a gaseous mixture. The physical separation material can be a molecular sieve with pores of uniform size and essentially the same molecular dimensions. These pores selectively adsorb molecules in accordance with molecular shape, polarity, degree of saturation, and the like. In the preferred embodiment, the physical separation medium is an aluminasilicate composition with 4 to 5 A (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13x zeolite. The zeolite adsorbs nitrogen, carbon monoxide, carbon dioxide, water vapor, and other significant components of air.

A cross-over valving means 20, which preferably includes a four-way valve 21, selectively and cyclically connects the inlet end of two beds, one at a time, during a production phase with a source of the gas mixture, e.g., air under pressure supplied from a first compressor 22 (i.e., the feed compressor), while the other bed is vented to atmosphere during a purge phase. Specific to the preferred embodiment, the cross-over valving means selectively connects one of the beds in fluid communication with an air pump or compressor 22 which supplies air from about 15 to about 21 psi. As used herein, "fluid communication" refers to means allowing flow of the appropriate gases. Of course, vacuum can also be used during the purge phase with the present invention to enhance evacuation. Compressor 22, which receives air from inlet 23, is connected to a first drive motor 25, in the preferred embodiment about a ¼ horsepower electric motor. A solenoid (not shown) or other cross-over valve actuating means selectively causes the cross-over valving means to move alternately between first and second positions. In the first position, the first bed 10 is connected with compressor 22 to cause nitrogen adsorption and oxygen enrichment in the product gas, and the second bed 12 is vented to atmosphere to allow evacuation. In the second position, the first bed is vented to atmosphere to allow evacuation and the second bed is connected with the air compressor to cause nitrogen adsorption. The invention is described with specific reference to a pressure-swing control. However, it is equally applicable to other methods of sequencing the gas flow through the sieve beds such as a timing-based system.

The composition of the gas in the voids of the zeolite varies from substantially pure primary-product gas at the outlet end, to the ambient gaseous mixture composition at the inlet end. As the gas mixture is introduced through a bed inlet to an adsorbed, gas-free or regenerated bed, an adsorption zone of finite, relatively large size is formed. This adsorption zone is a region of the bed in which the fill capacity of the adsorbent to hold the adsorbable components has not been reached. This adsorption zone moves from the bed inlet toward a bed outlet with a velocity significantly less than the superficial gas velocity in the bed. When the adsorption zone reaches the outlet end of the bed, adsorbable components begin to flow through the bed outlet into the nonadsorbable primary product stream. This time is hereinafter referred to as the "breakthrough." For a given gaseous composition, the breakthrough is defined by the size and configuration of the bed container as well as the packing configuration of the molecular sieve and the flow rate and bed gas pressure. The configuration of the bed is generally cylindrical and the output volume rate can vary from about 0.1 to 6 liters per minute. The breakthrough is the time required for the diffusion reaction as the nitrogen saturates and is weakly bonded to the sieve bed. When breakthrough occurs, primary product-enriched bed gas in the zeolite voids varies from a higher primary product gas concentration at the bed outlet to a lower concentration at the bed inlet. In the preferred embodiment, the primary product-enriched bed gas is about 80 percent primary product at breakthrough. While adsorption is occurring in one bed, the adsorbable components adsorbed by the separation medium of the other bed are purged from the other bed because of the drop in pressure due to atmospheric venting and because of exposure to relatively pure product gas from the first tank.

The first bed 10 is connected with a reservoir or product tank 30 by way of a first check valve 32 or other unidirectional valving means. The first check valve 32 permits the primary product gas from the first bed 10 to flow into the reservoir or product tank 30 via line 46 when the product gas pressure in the first bed 10 exceeds the pressure of product gas in the reservoir or product tank 30. The first check valve prohibits the product gas from flowing from the reservoir or product tank 30 when the pressure in the first bed 10 is lower than the reservoir or product tank. More specific to the preferred embodiment, the check valve imposes a 1.5 psi bias such that flow is only permitted when the pressure in the first bed exceeds the pressure in the reservoir or product tank by 1.5 psi. The second bed 12 is connected with the reservoir or product tank 30 by way of a second check valve 34 or other unidirectional valving means. The second check valve 34 again provides for unidirectional flow of the primary product gas from the second bed 12 to the reservoir or product tank 30.

A pressure equalization flow path 40 extends between outlets of the first and second beds. A concentration equalization valve 42 is either open or closed to selectively permit or prevent gas flow through the flow path between the first and second beds. A control means 50 cyclically causes the cross-over valve actuating means (i.e., two solenoids) and the concentration equalization valve 42 to be operated. The control means periodically and cyclically enables a concentration equalization valve actuator which is also a solenoid.

Oxygen sensor 43 registers the oxygen concentration of the product gas and can be located in the product tank 30. The sensor 43 communicates a sensed value to the microprocessor (i.e., control means). Similarly, a pressure sensor 45 registers the pressure in the product tank and communicates the same to the microprocessor.

The control means causes the cross-over valving means 20 to alternate between its first and second positions for the appropriate period during each cycle segment. A cycle segment can be either the product gas generation cycle or the purge cycle. The cycle duration is selected such that each bed is connected with the source of air for a period of time which is equal to or less than the breakthrough time. The mechanism which triggers the cross-over valving can be based on the pressure, such as a pressure set point or set point range, in the bleed line from the product tank as is used in a pressure-based control cycle, or it can be based strictly on a residence time from the product-producing bed, such as in a timing cycle-based control cycle. In accordance with another embodiment of the invention, the control cycle can utilize variable pressure in order to achieve a residence time within a defined range based upon a projected breakthrough time. In the preferred embodiment, the beds are 3.5 inches in diameter, 15 inches in length, and each contains 6.5 pounds of 5A zeolite.

The gas mixture is supplied at up to 21 psi of pressure to the first bed. Concurrently, the second bed (i.e., a "used" bed) is vented to atmosphere to cause purging of the nitrogen-enriched molecular sieves. Before the breakthrough time, the concentration equalization valve is opened allowing primary product-enriched gas from the first bed to flow into the evacuated second bed. During the concentration equalization period, one bed is evacuated and the other has just reached the pressure set point which drives flow between the beds. The flow is of high oxygen content so that the first product to pass into the product tank via line 46 is essentially product gas produced by the oxygen beds. The second bed pressure is product-enriched gas to purge the sieve bed. Before the primary product-enriched gas from the first bed is evacuated through the second bed, the cross-over valving means 20 is actuated to reverse its position. Actuating the cross-over valving means discontinues supplying of the gaseous mixture to the first bed and commences evacuating it and concurrently discontinues evacuating the second bed and commences supplying it with the gaseous mixture.

Subsequent to the actuation of the cross-over valving means, the concentration equalization valve 42 remains open to continue allowing a purge supply of product-enriched gas to flow into the second bed. This equalizes the concentration of gas which is supplied to the product tank since the cycling is sequenced so that the product gas proceeds from the breakthrough zone to flow into the product tank. Subsequently, the concentration equalization valve closes and terminates the flow of primary-product gas between the beds. In the second segment of the cycle, the pressure in the second bed increases approaching the gas mixture source pressure. Concurrently, the pressure in the first bed decreases approaching atmospheric pressure. Before the secondary product molecules have traversed the second bed, the concentration equalization valve 42 is opened allowing the primary product-enriched gas in the zeolite voids of the second bed to flow to the first bed. While the primary product-enriched gas is flowing to the first bed, the cross-over valving means is actuated. Actuating the cross-over valving means discontinues the evacuation of the first bed and commences supplying the gaseous mixture and concurrently discontinues supplying the gaseous mixture to the second bed and commences evacuating it. Subsequent to actuating the cross-over valving means, the concentration equalization valve is closed terminating the pressure equalizing flow of the primary product-enriched gas between the beds. The steps are cyclically repeated to provide continuing fractionating of the primary product gas from the mixture.

Referring again to FIG. 1, in a preferred embodiment the reservoir or product tank 30 maintains a reservoir of oxygen at a minimum pressure of about 14 psi. The oxygen-enriched gas contains from about 50 to about 99 percent, desirably from about 70 to about 98 percent, and preferably from about 84 to about 96 percent by volume of oxygen. In accordance with conventional procedures, product tank 30 can be connected to a pressure regulator (not shown) for controlling the pressure of the oxygen to a patient. Typically a pressure of 5 psi is utilized. A flow meter (also not shown in FIG. 1) can be utilized to limit the flow rate to the patient such as from 0.1 to about 6 liters per minute with a flow rate of about 3 liters per minute often being utilized. If desired, a humidifier (not shown) can add moisture to the oxygen-enriched gas. The gas is delivered to the patient via tubing and breathing apparatus which can be inserted into the patient's nostrils.

In accordance with other concepts of the present invention, oxygen-enriched gas from an oxygen concentrator such as that described hereinabove can be fed in any variety of methods to a compressor where it is compressed to very high pressure and stored in a portable or mobile container such as a gas cylinder.

Figure 2:
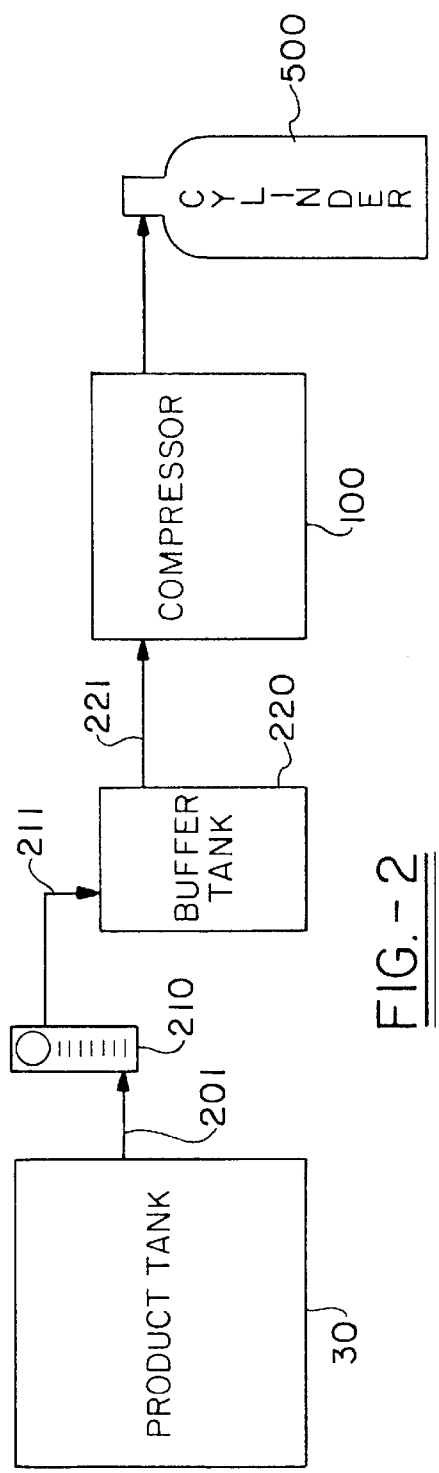
FIG. 2 is a block diagram of an apparatus and process in accordance with the present invention for compressing oxygen-enriched air and feeding it to a portable container.

In the embodiment of FIG. 2, all of the oxygen-enriched gas is fed to a compressor. A concentrator (not shown but such as described hereinabove) has an oxygen-enriched product tank 30 wherein the pressure can vary as from about 14 to about 21 psi. The oxygen-enriched gas therein is fed via line 201 to a flow meter 210 at the pressure of the concentrator tank, that is from about 14 to about 21 psi. Flow meter 210 controls the flow rate of the oxygen-enriched gas which is fed via line 211 to buffer tank 220 wherein the gas pressure therein can also range from about 14 to about 21 psi. Via line 221, the predominantly oxygen gas is fed to compressor 100. Compressor 100, in a manner described below, compresses the oxygen-enriched gas to a pressure of about 2,250 psi and stores it within a mobile or portable cylinder 500. Depending upon the withdrawal rate of the oxygen-enriched gas by the compressor, the feed pressure thereto can range from 21 psi down to a predetermined cut-off pressure such as about 5 or 7 psi whereupon the compressor is automatically shut off by a pressure sensor switch.

Figure 3:
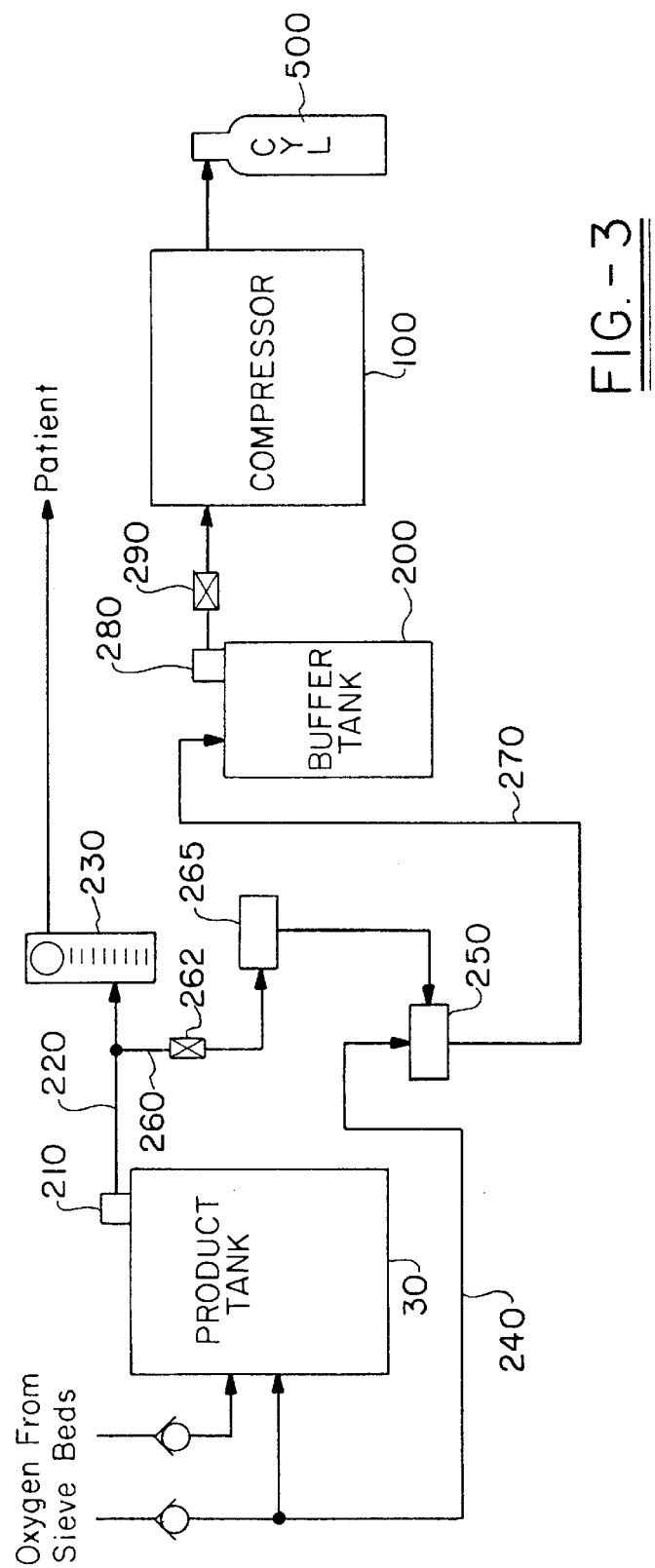
FIG. 3 is a block diagram of the apparatus and process of the present invention for feeding a portion of enriched gas at a controlled rate to a patient and another portion of the enriched gas to a compressor for high-pressure storage in a portable container.
Figure 4:
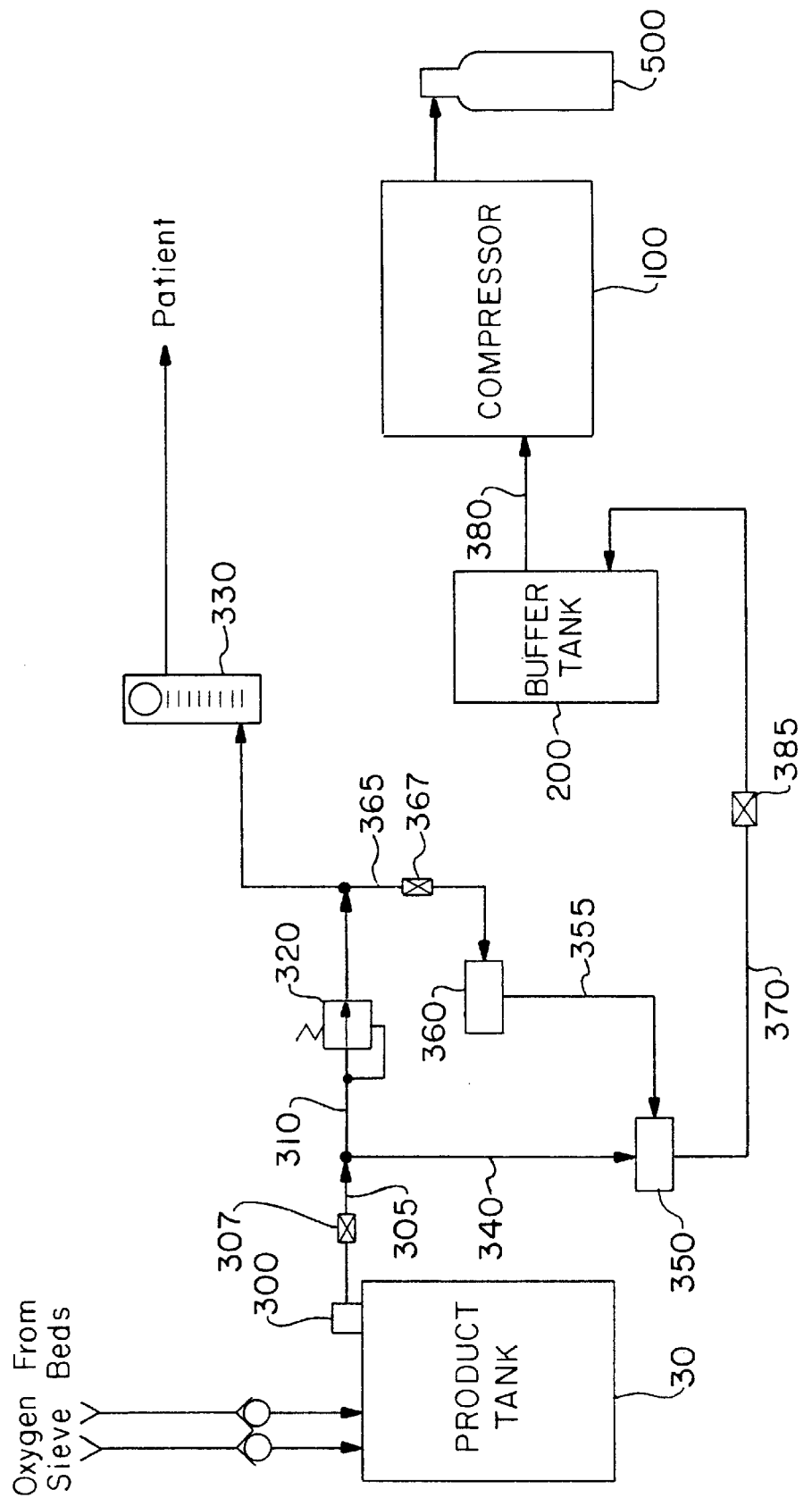
FIG. 4 is a block diagram of the apparatus and process of another embodiment of the present invention for feeding a portion of enriched gas at a controlled rate to a patient and another portion of the enriched gas to a compressor for high-pressure storage in a portable container.

FIGS. 3 and 4 relate to embodiments wherein oxygen-enriched air from product tank 30 of the oxygenator is fed by various methods desirably to a buffer tank of the compressor but prioritized as with regard to oxygen concentration and/or a sufficient pressure. For example, the feed rate to a patient can vary from between 0.1 and 6 liters per minute at a pressure of a predetermined value such as 5 psi with the remaining oxygen-enriched gas generally being fed at a different pressure to the buffer tank. The buffer tank can generally contain a broad range of pressure therein such as, for example, between 14 and 21 psi. However, as noted with regard to FIG. 2, depending upon the withdrawal rate of the gas in the buffer tank by the compressor, the pressure thereof can drop down to a predetermined cut-off pressure, such as 7 psi, which is higher than the pressure of the gas being fed to the patient to ensure an adequate flow of the oxygen-enriched gas to the patient.

Referring to the embodiment of FIG. 3, a 5-psi regulator 210 emits oxygen-enriched gas from product tank 30 into flow line 220 and feeds the same to flow meter 230 which subsequently emits the oxygen-enriched gas to the patient at a predetermined flow rate of from 0.1 to 6 liters per minute. Optionally, the flow meter can be closed so that all the enriched oxygen is directed to the compressor. Gas not directed to the patient is carried via line 240 to two-way valve 250. A very small portion of the gas in line 220 is directed through line 260 through restrictor 262 into oxygen sensor 265 which detects whether or not the concentration of the oxygen is of a predetermined value such as is at least 84 percent. When the oxygen sensor detects a concentration at or above the predetermined level, two-way valve 250 is open and permits the oxygen-enriched gas to flow through line 270 into buffer tank 200 wherein the pressure is essentially the same as the oxygen product tank pressure. However, should the oxygen sensor not detect a suitable oxygen concentration, two-way valve 250 is closed so that the oxygen concentrator can build up a sufficient oxygen concentration. This arrangement prioritizes the flow of oxygen-enriched gas so that the patient is assured of receiving a gas having a minimum oxygen concentration therein. Buffer tank 200 can have a regulator 280 thereon generally set at 12 psi to admit the oxygen-enriched gas to the compressor when needed. Alternatively, the pressure regulator can be set at anywhere from about 13 to about 21 psi. Restrictor 290 controls the flow rate of gas from the buffer tank to the compressor. Should the compressor drop the pressure in the buffer tank to below a predetermined value, a pressure sensor (not shown) will automatically cut off the flow of gas at a pressure above the pressure of the gas being fed to the patient. This prioritization assures that the patient receives priority with regard to oxygen-enriched gas.

The embodiment of FIG. 4 emits the oxygen-enriched gas through a 14 to about an 18-psi regulator 300 into flow line 305 having flow rate restrictor 307. The flow is then split with a portion via line 310 going through 5-psi regulator 320 and into flow meter 330 which then directs the gas to the patient at a desired flow rate of generally from 0.1 to 6 liters per minute, although optionally the flow meter can be closed. The remaining portion of the gas is directed via line 340 to two-way valve 350. A small portion of the gas going to the patient is diverted through line 365 through flow restrictor 367 to oxygen sensor 360. As in FIG. 3, the oxygen sensor is set at a predetermined value such as a concentration of 84 percent so that when the level is not achieved, two-way valve 350 is closed through electrical line 355. This aspect allows the amount of oxygen in the concentrator tank to be increased by the oxygenator unit. The same prioritizes the concentration of oxygen to ensure that the patient receives an amount of oxygen of at least the minimum predetermined value. When the oxygen concentration is sufficient, the gas flows through two-way valve 350 into line 370 and into buffer tank 200 where it is stored generally at a pressure of about 14 to 18 psi. A relief valve 385 which can be set at any desired value such as about 14 psi ensures that gas under sufficient pressure is being admitted to the buffer tank. The oxygen-enriched gas is admitted to the compressor via line 380. Should the compressor withdraw gas faster than it is being received by the buffer tank, the pressure therein will drop. A pressure sensor switch (not shown) can be set to a predetermined value (e.g., about 7 psi) to ensure or prioritize that a sufficient amount or flow of gas is being fed to the patient. The predetermined shut-off pressure of the compressor is always above the pressure of the gas being fed to the patient. The embodiment of FIG. 4 is preferred.

While the above description, as exemplified by FIGS. 2, 3, and 4, generally constitutes a preferred embodiment of the present invention, it is to be understood that the same can be modified. For example, oxygen product tank 30 need not be utilized. Instead, the oxygen-enriched air from an oxygen concentrator, such as shown in FIG. 1, can be fed to the buffer tank via the shown and described flow lines of the various embodiments such as set forth in FIGS. 2, 3, and 4. Accordingly, the oxygen-enriched air will be separated with one component directed to the patient and the other component being directed to the buffer tank. Prioritization of the oxygen enriched gas to the patient either by a minimum oxygen concentration or a sufficient pressure in the buffer tank is still generally utilized. Alternatively, an enriched oxygen product tank 30 can be utilized and the buffer tank can optionally be eliminated. In other words, enriched oxygen from the product tank can be fed via one component to the patient and to a second component via the flow line shown to the compressor. In this situation, prioritization of the desired flow and oxygen concentration to the patient is maintained as described hereinabove with regard to either the level of oxygen concentration or an adequate pressure being admitted to the compressor.

Figure 8:
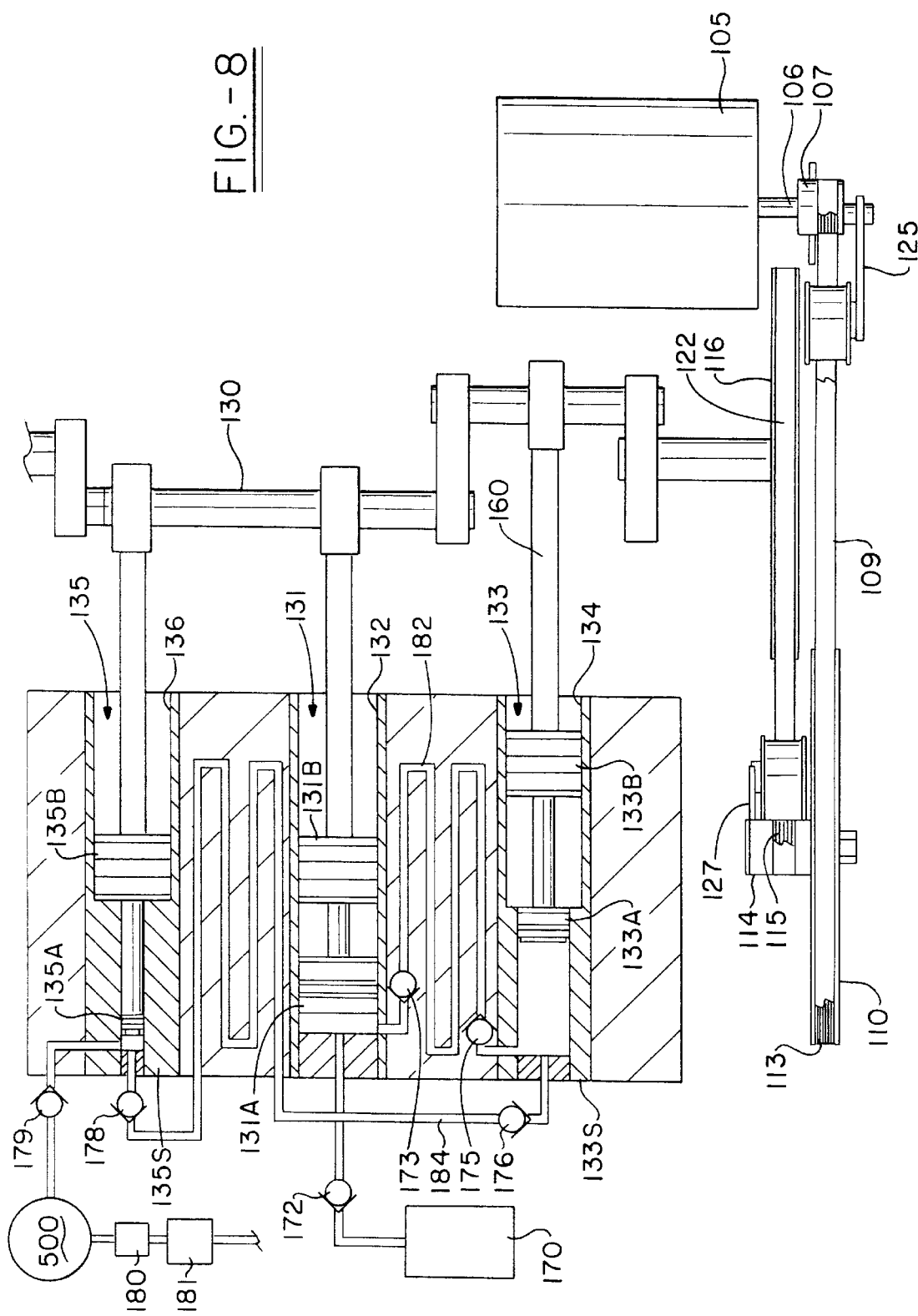
FIG. 8 is a top plan view of the compression apparatus of the present invention.

Referring now to the compressor assembly 100 as shown in FIGS. 7 and 8, it generally utilizes an AC electric-drive motor 105 which can rotate at any desired speed, e.g., 1,700 rpm. Motor 105 can contain a fan (not shown) either within the motor housing or immediately adjacent thereto to draw air through the motor to cool the same. Power is conveyed from the motor through shaft 106 to drive wheel 107. Desirably the drive wheel has a plurality of grooves therein to receive a V-belt such as main drive belt 109. Such belts are generally reinforced with fiber and have a very long life. Main drive belt 109 is connected to main gear 110 which contains a plurality of grooves 113 therein. The number of peripheral grooves 113, as well as the size and location thereof, coincides with the grooves of drive wheel 107 and matingly engage a plurality of projections located on main drive belt 109. Extending from main gear 110 is an offset hub gear 114 which has a much smaller diameter than main gear 110. Hub gear 114 also has grooves 115 thereon to receive a secondary drive V-belt 122. A second or secondary large gear 116 has grooves on the periphery thereof which matingly engage the secondary drive V-belt 122. Offset hub 114 through the secondary V-drive belt 122 contacts and serves to drive secondary gear 116 which in turn is connected to crankshaft 130.

Through the utilization of the two large gears 110 and 116, a double-reduction is obtained such that the rotational speed of crankshaft 130 is a desirably low speed such as approximately 50 rpm. Both drive belts 109 and 122 desirably have a spring-loaded idler arm 125 and 127, respectively, which applies a small amount of tension. The actual pull tension of the first belt can be about 20 pounds, whereas the tension on the second belt can be about 100 pounds.

The multi-stage compressor of the present invention can have any number of pistons, but in the present embodiment has three. As shown in FIG. 8, two of the pistons, i.e., the first and third pistons, are located on the same crankshaft lobe, whereas the second piston is located on a different lobe offset 180° from the first and third pistons. The reason for this is that pistons one and three will be drawing in air when the second piston is being compressed and vice versa Although not shown, a crankshaft can be utilized which contains three lobes thereon, each offset from one another by approximately 110° to 130°, e.g., about 120°, so as to minimize the torque resistance applied to the motor during the compression stroke.

The compressor of the present invention has three pistons, i.e., piston #1 (131), piston #2 (133), and piston #3 (135). Each piston is contained within a separate cylinder and thus piston #1 is contained within the first cylinder (132), the second piston is contained the second cylinder (134), and the third piston is contained within the third cylinder (136). While the diameter of the head 140 of the first piston is approximately equal to the diameter of the base portion of the piston as shown in FIGS. 8 and 9, the diameter of the head of piston #2 (133) is smaller than that of piston #1, and the diameter of the head of piston #3 (135) is smaller than the diameter of piston #2 (133). However, the base of each piston 131B, 133B, and 135B is of the same size for reasons set forth hereinbelow. In order to permit pistons #2 and #3 to operate properly, each contains an annular sleeve 134S and 136S on the inside of the cylinder wall the internal diameter of which is approximately equal to the external diameter of piston heads #2 and #3 respectively.

Regardless of the size of the piston head, it has two rings as generally indicated in FIG. 9. Inasmuch as the rings of all three piston heads are generally the same, only the first piston is shown in FIG. 9. The piston head has two annular grooves or recesses therein, that is top piston annulus 141 and bottom annulus 144. The top annulus contains a U-shaped seal therein generally made out of a Teflon® alloy or other low-friction material. The seal contains a coil tension spring 143 therein which forces the seal radially outward against the cylinder wall to prevent compressed air from leaking through the piston head between the piston and the cylinder wall. To also ensure the maintenance of a good seal, seal 142 is U-shaped so that upon the build-up of pressure in the cylinder head, the compressed gas will communicate and enter into the seal and force the outer edge thereof radially outward against the cylinder wall. Piston head bottom annulus 144 contains a flat or vertical glide ring 145 which extends around the annulus and is also radially forced outwardly by a coil tension spring 146 located therein. The bottom glide ring 145 can be made out of a Teflon® alloy and serves as a piston glide ring.

Connecting rod 148 connects the piston head to piston base 150. The piston bases of all three pistons are the same diameter and accordingly engage a mating cylinder of essentially the same diameter. The piston base contains an upper base annulus 151 and a lower base annulus 155, both of which have a glide ring therein similar to if not identical to glide ring 145 of piston head annulus 144. Thus, upper base annulus 151 has a glide ring 152 therein which is forced radially outward by coil spring 153. Similarly, lower base annulus 155 has a glide ring 156 therein which is radially forced out by coil spring 157. Although three glide rings have been shown and described as being identical, they can be different and use different material, and the like. Piston base 150 contains bore 158 which extends laterally therethrough. Bore 158 receives wrist pin 159. The wrist pin and coil spring both serve to maintain glide ring 156 in a radially outward position so as to bear against the cylinder wall.

The two-part piston assembly of the present invention contains bottom connecting rod 160 as shown in FIG. 10. The connecting rod contains a top bore 161 through which wrist pin 159 extends. Bottom bore 163 of the connecting rod extends about and matingly engages an appropriate portion of the crankshaft. In order to permit rotation of connecting rod 160 about the crankshaft 130, sealed portion 164 of the connecting rod contains bearings therein.

The net result of the two-part piston ring assembly of the present invention is that bearing 164 of connecting rod 160 can freely rotate with the crankshaft in a rotary or circular motion whereas top bore 161 moves in only a linear or reciprocal motion allowing piston rod 148 with the piston head and base thereon to move only in a linear reciprocating direction. The same thus prevents lateral forces from being applied to the cylinder wall which often results in wear and can create an oval-shaped cylinder wall. The two-part piston ring assembly of the present invention thus promotes long life of the piston and cylinder wall.

Although each piston serves to compress the gas admitted therein to a higher pressure, a desirable aspect of the present invention, as noted above, is that each subsequent piston head has a smaller area. For example, piston #1 (131) can have a diameter of approximately 1¾ inches, whereas piston #2 has a diameter of approximately 1¼ inches, and piston #3 can have a diameter of approximately ½ inch, which can be the diameter of essentially piston rod 148. Desirably, the increase in pressure from each stage or piston is proportional to the others. The compression ratio of each piston can vary, but generally is the same. Although compression ratios of up to 10 can be utilized, the desirable pressure range is from approximately 6 to about 8.

Inasmuch as heat is built-up during compression of the oxygen-enriched gas, the flow lines between the pistons can be extended so that they are long enough to permit the heat of compression to be absorbed by ambient air and thus cool the enriched pressurized gas therein. As shown in FIG. 8, cooling line 182 from the first piston to the second piston can be in the form of an undulating path or the like and the same is true with regard to cooling line 184 between the second and third pistons.

The operation of the compressor portion of the apparatus is as follows. Electric motor 105 which operates independently of the compressor feeding air to the molecular sieves in the oxygen concentrator portion of the apparatus, through drive belts 109 and 122, rotates crankshaft 130 thereby causing piston #1, #2, and #3 (131, 133, 135) to reciprocate and compress air in their respective chambers. More specifically, enriched oxygen gas from the compressor buffer tank is fed to the first piston. Piston 131 contains an inlet check valve 172, which permits air to enter the cylinder head space above the piston, and outlet check valve 173, which permits the compressed gas to exit from the first piston. The check valves permit flow of the gas in one direction so that once the gas is admitted to the first piston, during the compression stroke thereof it cannot be forced back out to the buffer tank. Similarly, once forced out of the first piston, outlet check valve 173 prevents the gas from being sucked in during the intake stroke of the first piston. In a similar manner, second piston 133 has an inlet check valve 175 which permits the compressed air from piston #1 to be drawn into the head space above piston 133, but prevents it from being forced back into the first piston. Outlet check valve 176 prevents the gas compressing the second piston from being drawn back into the piston once it has been expelled therefrom. In a similar manner, the gas which has been further compressed in piston #2 is fed into piston #3 (135) through inlet check valve 178 where it is further compressed. The compressed gas is then fed through outlet check valve 179 into enriched oxygen gas storage cylinder 500. Outlet check valve 179 thus prevents the highly compressed stored gas in the cylinder from being admitted back into the third piston.

During the operation of the compressor, the gas in portable cylinder 500 which is initially at ambient pressure, is gradually built up to desired pressure. One such suitable pressure is approximately 2,250 psi. Of course, different cylinders can accept either higher or lower gas pressures and readily maintain the same. Rupture disk 180 is a safety feature designed to rupture at a pressure in excess of the desired storage pressure of the gas cylinder. Thus, in the present embodiment, such a pressure can be approximately 2,800 psi. Although not shown, rupture disks can also be provided in the flow lines from the exit of the first and second cylinders to prevent undue build-up in these lines. A pressure regulator 181 serves to emit the oxygen enriched gas at a pressure of about 5 psi to a patient via a flow meter (not shown) at any desired rate, such as from about 0.1 to about 6 liters per minute.

As previously noted, the buffer tank contains oxygen-enriched gas at a pressure of generally from about 7 or 14 psi to about 21 psi. The compressor is designed to commence compression generally when the pressure in the tank is generally at a maximum until it drops to a predetermined pressure, e.g., 7 or 8 psi. In general, the pressure is electrically controlled by various switches, sensors, relays and the like. Briefly, a master ON/OFF switch emits power to compressor motor 105 which in turn causes the crankshaft to rotate and compress air. Two pressure-sensitive switches exist: a low pressure sensor which detects pressure below a predetermined value, e.g., 7 to 12 psi, and a high pressure sensor which detects pressure above 2,250 psi. When the low pressure sensor detects pressure below the predetermined level, it will turn off motor 105 through a relay switch. This allows oxygen inflow from the concentrator to be built-up in the buffer tank to a desired pressure. The low pressure sensor is a solid-state relay. Should the relay fail, it will fail closed and allow the motor to continue to run. Accordingly, this relay switch is connected in series with the high pressure sensor mechanical relay switch which will shut the motor off when the pressure in the cylinder reaches approximately 2,250 psi.

Figure 6:
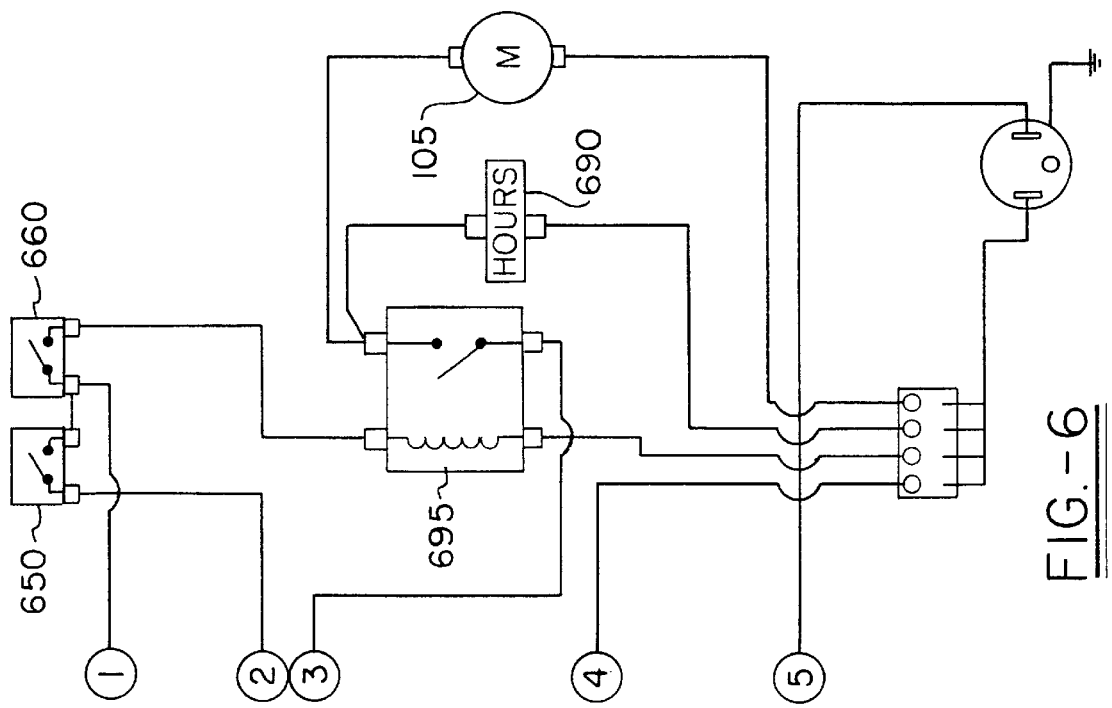
FIG. 6 is a schematic of the remaining portion of the control circuit of FIG. 5 for operating a multiple-stage compressor of the present invention.
Figure 5:
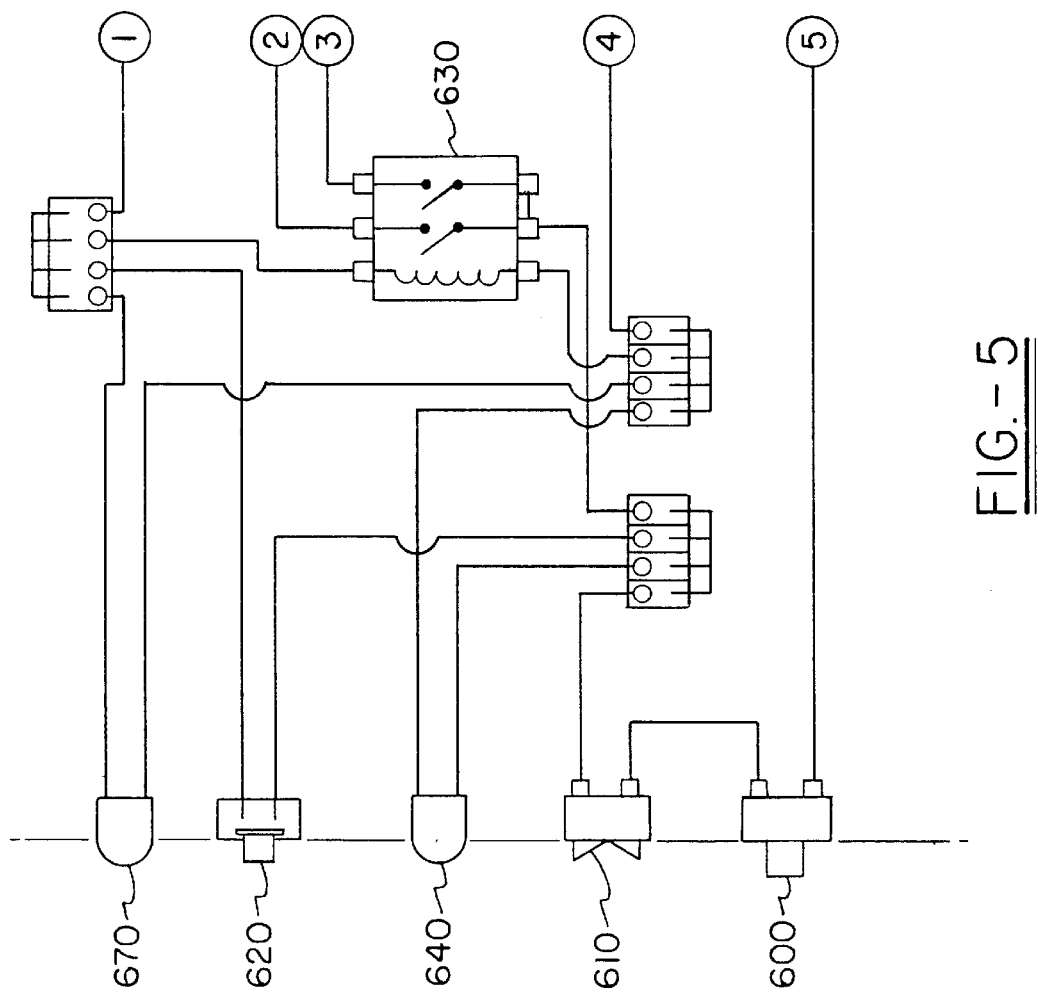
FIG. 5 is a schematic showing one portion of a control circuit for operating a multiple-stage compressor of the present invention.

FIGS. 5 and 6 show the electrical circuitry of the compressor. Power is fed to the compressor initially through the resettable breaker 600 and then to power switch 610. When the power switch is pushed to the "ON" position, power passes to the motor start switch 620, the start relay common contacts 630, and also lights the power indicator 640. When start switch is depressed, the start relay coil is energized which causes both switches of the relay to close.

One of these closed switches passes the power to high pressure switch 650 which is normally closed when the output pressure of the compressor is under 2,250 psi. The output of the high pressure switch is fed back to the start relay coil to keep the coil energized without the start switch being depressed, but will cut power to the coil when high pressure is reached. (This occurs when a tank has been filled.) The output of the high pressure switch is also connected to the common of low pressure switch 660. While the input pressure from the concentrator is above the pre-determined value, e.g., 7 psi, the low pressure switch is closed and the normally closed contact has power. This power signal is fed to the drive contact of the solid-state relay which, in turn, allows the solid-state output to be "turned on." The output of the high-pressure switch is also connected to the run indicator 670 which then lights up.

The second closed switch of the start relay is connected to the "input" of the solid-state relay. When the solid-state relay is turned on by the signal from the low pressure switch, power is passed to motor 105 and its start capacitors through the solid-state output. A common line is connected to the other side of the motor to complete the circuit. An hour meter 690 is wired in parallel to the motor to monitor motor run time.

When the above occurs, the motor beings to run and remains running until one of two conditions occur. The first condition would be the input pressure to the compressor falls below a predetermined value, e.g., 7 psi. This will cause low pressure switch 660 to open and solid-state relay 695 to turn off, which in turn shuts off motor 105. If the input pressure to the compressor rises above a desired predetermined pressure, low pressure switch 660 will close and once again turn on the solid-state relay and start the motor. This is a normal occurrence that is dependent upon concentrator efficiency and may be repetitive.

The second condition that will shut off the motor occurs when an oxygen tank has been filled. The output pressure will rise above 2,250 psi and therefore cause high pressure switch 650 to open. This cuts the power to the start relay coil which causes both switches to open and cuts the power to both the input of the high pressure switch and the input to the solid-state relay thereby shutting off the motor. To start the motor after this condition is reached requires start switch 620 to be depressed. If greater than 2,250 psi remains, the high pressure switch will remain open and no signal will be fed back to the start relay coil to keep it energized therefore causing the motor to remain off. While the high pressure switch is open, run indicator 670 remains off.

Any direct shorts between power and common or any condition that draws more than 8 amps of current will cause resettable breaker 600 to pop open.

As apparent from the above, the operation of compressor 100 is completely independent of the oxygen concentrator and utilization of gas compressed thereby as a power or energy source. In other words, the pressure accumulated in the oxygen concentrator is not utilized to drive or operate any pistons in the compression portion 100 of the apparatus.

A distinct advantage of the apparatus and method for forming oxygen-enriched gas and compression thereof according to the present invention is the creation of a mobile or portable source of gas containing high purity oxygen. Patients who require oxygen-enriched gas, as from about 80 to about 98 percent, are no longer confined to the vicinity of an oxygen concentrator as for example a bed, home, hospital, or a wheelchair. Rather, the patient can carry the mobile gas cylinder in any convenient manner, such as in a backpack, and thus can take trips via wheelchair, an automobile, and even planes and trains. Depending upon the pressure and size of the storage cylinder, the oxygen supply can be anywhere from about 2 to about 24 hours or even longer.

An alternative compact compressor 700 is shown in FIGS. 11 through 15 wherein the motor, drive wheels and drive belt assembly is similar to that shown in FIGS. 7 and 8. Motor 701 contains a shaft 702 which through first drive belt 703 is connected to first drive wheel 705 having first drive shaft 708. The drive wheel contains a plurality of grooves and projections to receive drive belt 703, which respectively includes corresponding projections and grooves. First drive shaft 708 is connected to hub gear 710. In order to transfer power from hub gear 710 to second drive wheel 715, second drive belt 713 is utilized which has a plurality of projections and grooves which engage, respectively, grooves and projections of second drive wheel 715. Second drive wheel 715 is connected to second drive shaft 718.

Due to utilization of motor 701, which generally can be any conventional electric motor capable of rotating at any desirable speed, for example, at about 1,600 or 1,700 RPM, with drive wheel 705 having hub gear 710 and second drive wheel 715 having second drive shaft 718, a double reduction of the rotational speed of the motor is achieved. The reduction ratio of the motor shaft speed to the first drive wheel or shaft 708 thereof and the reduction from the first drive shaft 708 to the second drive wheel and shaft 718 thereof can be any desirable value depending upon the diameter of the various drive wheels and hub shafts. Desirably the first reduction is approximately a ratio of 6:1 so first drive shaft 708 rotates at about 265 to about 285 RPM. The reduction ratio between the first drive shaft 708 or offset gear and the second drive shaft 718 is also approximately 6:1 so that the second drive shaft rotates at approximately 44 to about 48 RPM. Although not shown, both drive belts 703 and 713 can pass over spring loaded idler arms which apply a small amount of tension thereto and ensures tension between the various connective shafts or drive wheels. Alternatively, a toothed belt gear drive, etc., can be utilized which engages teeth located on the various drive wheels and hubs.

Figure 11:
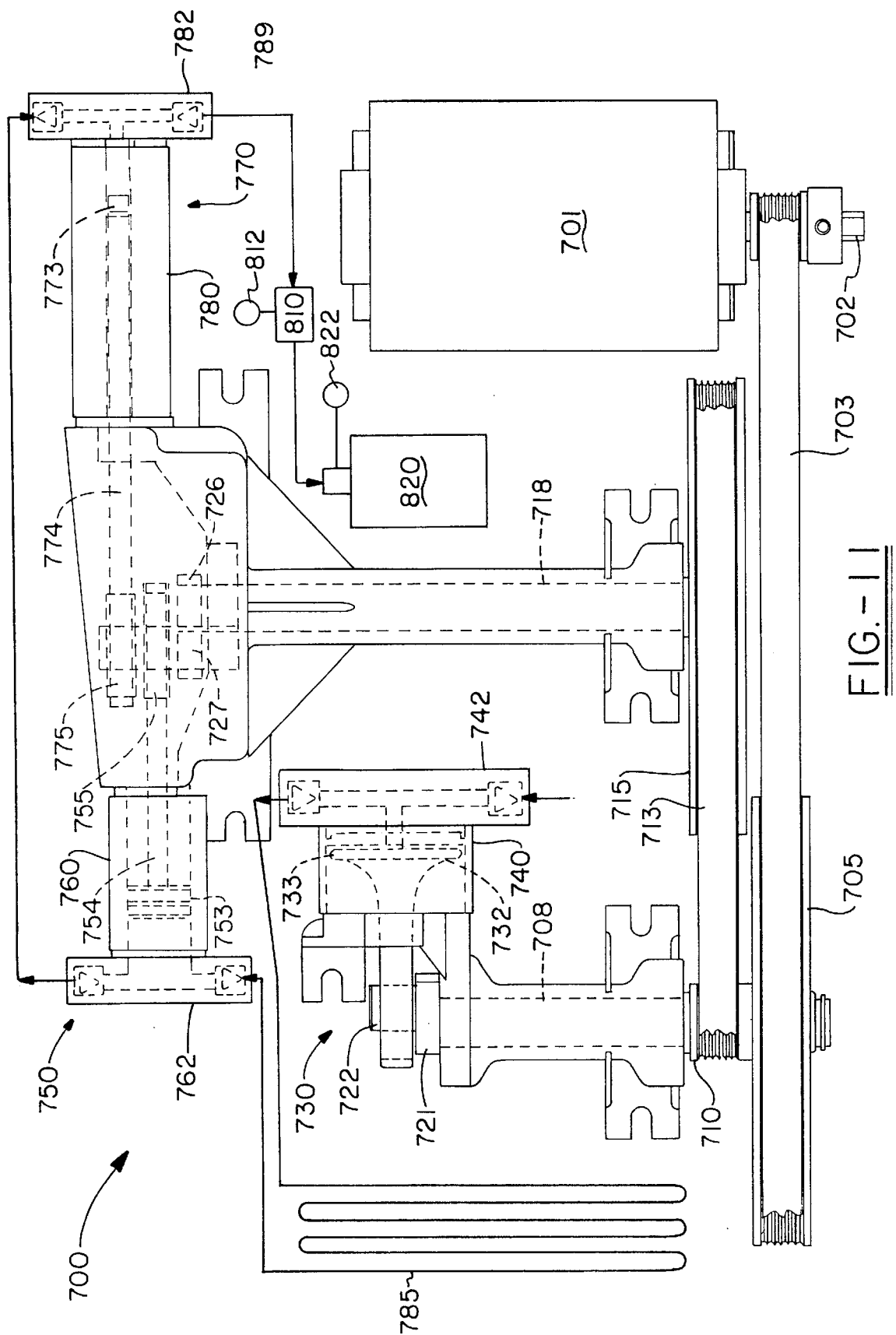
FIG. 11 is a top plan view of an alternate embodiment compressor apparatus of the present invention.
Figure 12:
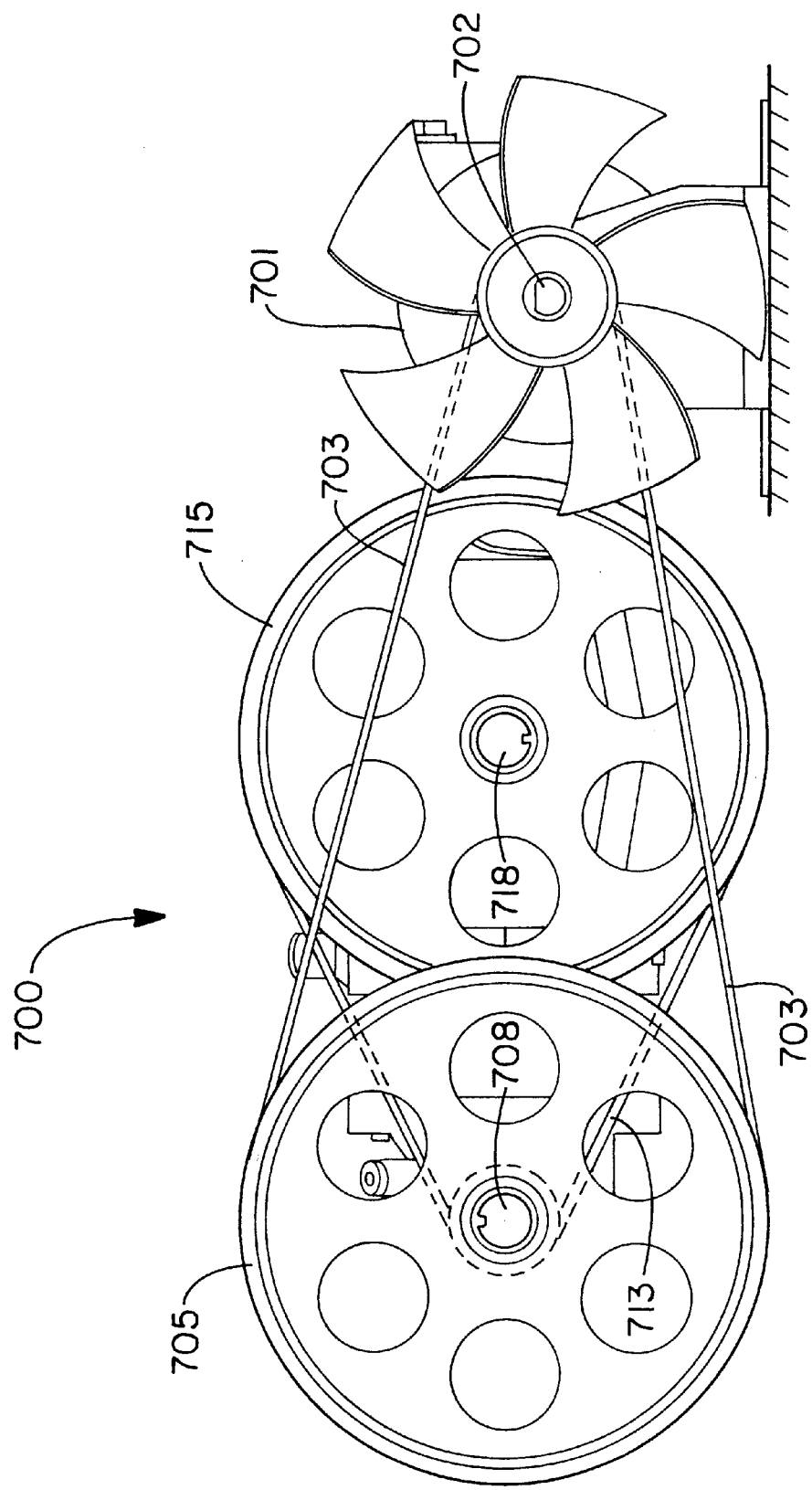
FIG. 12 is a front elevational view of the alternative compression apparatus shown in FIG. 11.
Figure 14A:
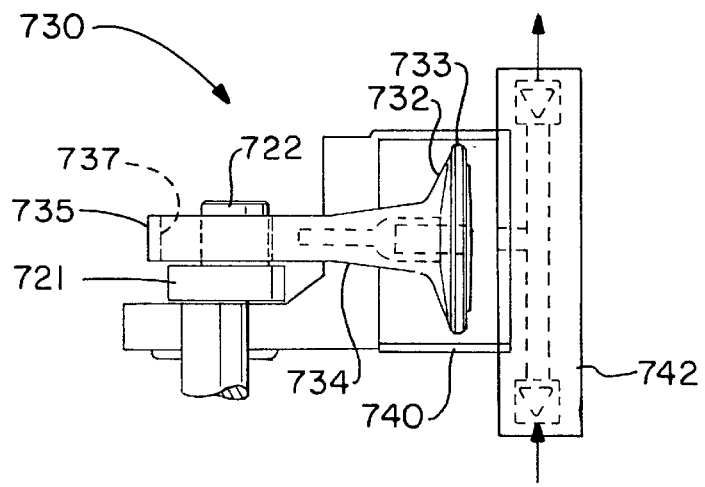
FIG. 14A is a partial plan view of a first piston of the present invention.

The compact compressor assembly 700 can generally contain any number of compression stages such as cylinders and pistons but desirably contains three as shown. The first piston desirably is a wobble piston which is connected in series with two sequential cylindrical pistons for compressing the oxygen enriched gas or other gas to a generally predetermined pressure. Considering wobble piston assembly 730, as seen in FIGS. 11 and 14A, it contains wobble piston 732 having a relatively large diameter head 733 thereon, which is fixedly connected by connecting rod 734 to base 735 having aperture 737 therein. The wobble piston is operated by first drive shaft 708 by means of offset cam 721 which has an offset shaft 722 extending therefrom. Offset shaft 722 engages wobble base aperture 737 to reciprocate the wobble piston. Since there is no pivot point in the vicinity of wobble piston head 733, as shaft 708 rotates wobble piston 732 will reciprocate in a longitudinal direction and at the same time wobble. That is, the top portion of the piston head or face will longitudinally proceed or recede the center point of the piston head due to offset cam shaft 722. The wobble piston assembly will compress enriched oxygen received from product tank 30 or the buffer tank 200 and compress it in piston cylinder 740 when received from cylinder manifold head 742.

The compact multi-stage compressor of the present invention can have more than one wobble piston assembly, although one is preferred. It can also have more than two cylinder piston assemblies, although two are preferred. As shown in FIG. 11, the second and third piston assemblies 750 and 770 are generally offset longitudinally aligned and operatively connected to second drive shaft 718 so that as the gas, such as enriched oxygen, is being compressed in one cylinder, the gas in the other cylinder is being drawn therein. Second drive shaft 718 has an offset cam 726 located at the end thereof which cam contains offset cam shaft 727 to which both piston assemblies 750 and 770 are connected.

Figure 13:
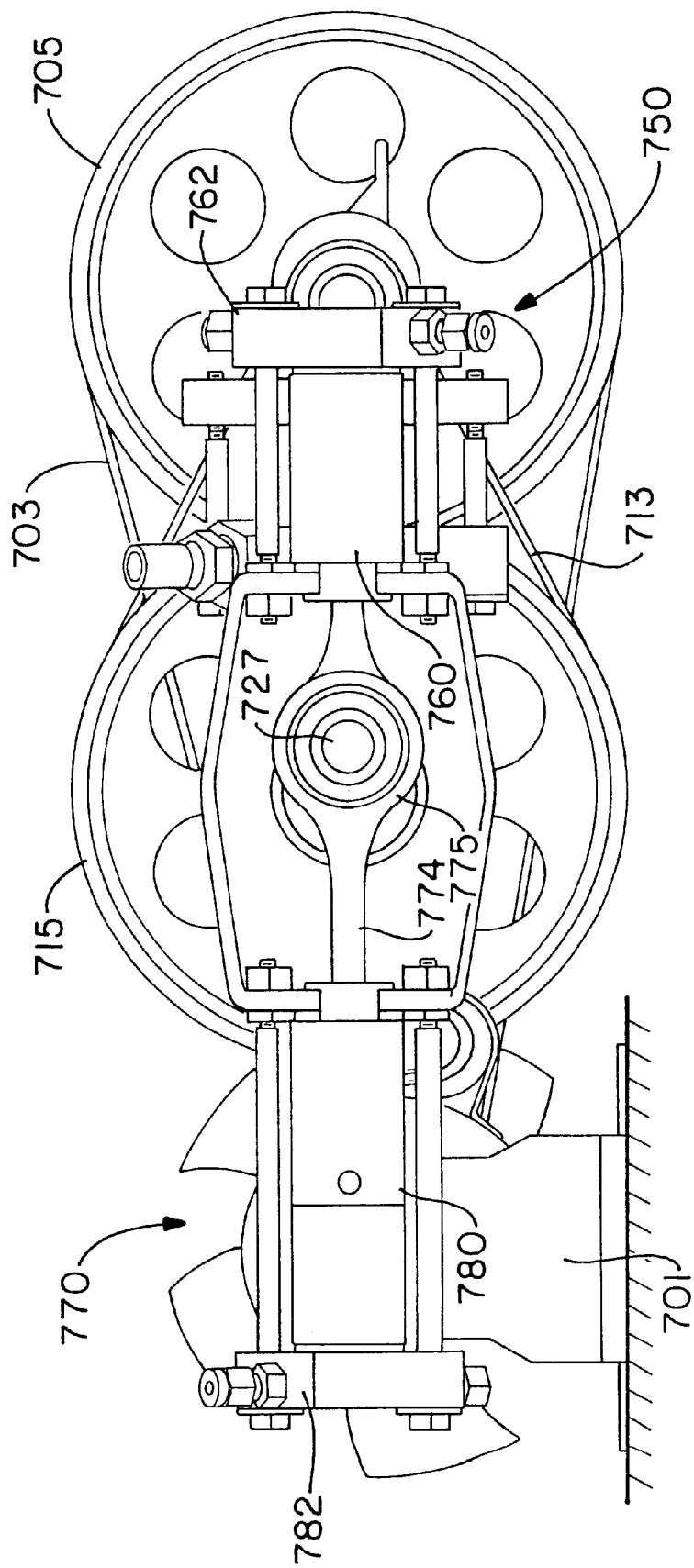
FIG. 13 is a rear elevation view of the alternative compression apparatus shown in FIG. 11.

The structure of the second and third cylinder assemblies is generally shown in FIGS. 11 and 13. Second piston assembly 750 contains piston head 753, which is pivotally connected through a wrist pin, not shown, to connecting rod 754. Base 755 of the connecting rod through an aperture is pivotally connected to offset drive shaft 727. The piston reciprocates within second cylinder 760 which contains cylinder manifold 762 to admit and release the oxygen or gas from the cylinder. Upon compression of the oxygen or gas in the second cylinder, it is transferred to the third piston assembly 770 via line 787.

Similarly, third piston assembly 770 contains piston head 773, which through a pivotal wrist pin, not shown, is connected to connecting rod 774. Connecting rod base 775 has an aperture therein which pivots about offset drive shaft 727. The piston assembly is contained within third cylinder 780. Cylinder manifold 782 receives enriched oxygen or gas via transfer line 787 from the second cylinder and after compression thereof; the compressed oxygen or gas is transferred by line 789 to a high-pressure storage container such as a bottle cylinder 820.

Figures 14B, 14C:
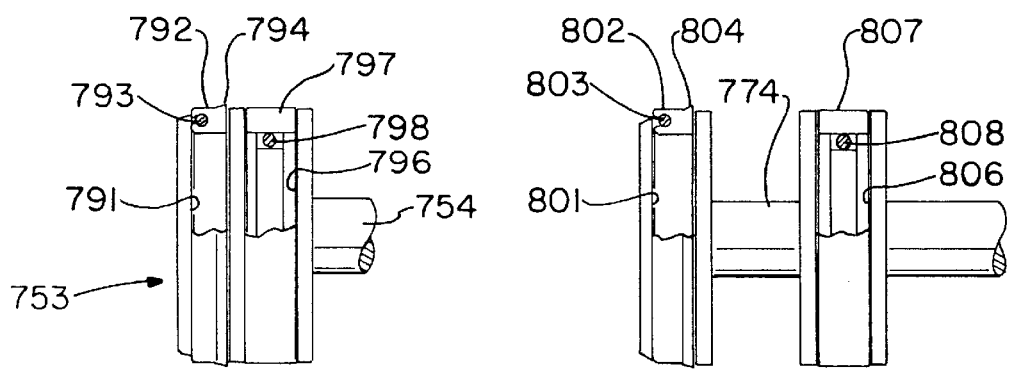
FIG. 14B is an enlarged partial elevation view of the second piston of the present invention.
FIG. 14C is an enlarged partial elevation view of the third piston of the present invention; and, FIG. 15 is an electrical schematic of the various circuits for controlling the compact compressor.

The piston rings of the second piston head 753 are shown in FIG. 14B, enlarged for clarification, and contain a first annulus 791 which has U-shaped seal 792 therein. A tension coil spring 793 resides within the U portion of the seal and serves to force the seal radially outwardly against the walls of the cylinder. The base of the seal 794 extends radially outward to further effect a seal with the cylinder wall. A second annulus 796 contains a glide ring 797 therein which is forced outwardly against a cylinder wall by coil spring 798. The third piston head is similar to the second piston head but the two seals are separated from each other by connecting rod 774 as seen in FIG. 14C. Thus, a first annulus 801 has a U-shaped seal 802 therein containing tension coil spring 803 which forces the seal radially outward against the piston wall. As in FIG. 14B, base 804 of the first seal extends radially outward against the cylinder wall. Separated by connecting rod 774, a second annulus 806 in the piston head contains glide ring 807 which is forced radially outward against the cylinder wall by coil tension spring 808. The configuration of the seals of the second and third pistons help maintain a tight seal during operation assuring that compression is not lost.

The compact and lightweight compressor assembly 700 can achieve any desirable final pressure (e.g., from about 500 to about 3,000 PSI) such as that required for a compressed gas container and especially a compressed oxygen enriched bottle for use by a patient. In the embodiment shown and described, a final pressure of approximately 2,000 PSI is often preferred. Accordingly, wobble piston 732, while having a short stroke but a large piston head, generally receives enriched oxygen from product tank 30 or buffer tank 200 through a restrictor at any desired pressure such as about 10 PSI and compresses it to about 60 PSI. Desirably, there is an accumulator tank 785 between the first piston assembly and the second piston assembly 750 to store up the compressed gas produced by the wobble piston inasmuch as it reciprocates approximately six times for every one reciprocation of the second and third pistons. This tank can be a conventional tank such as a cylindrical tank, or desirably it can be in the form of a long thick but wide hose 785. Compressed gas from the wobble piston assembly, which is operated by first power source 705, is transferred to second cylinder manifold 762, where it is compressed by the second piston, operated by second drive shaft 718, to a pressure of approximately 400 PSI. From there it is transferred via line 787 to the input of third cylinder manifold 782 whereupon it is compressed by the third piston, which also is driven by second drive shaft 718, to a pressure of approximately 2,000 PSI.

To achieve the desired increase in pressure, the diameter of each subsequent piston head is generally decreased. It is to be understood that generally any desirable head diameter can be utilized. In the embodiments of FIGS. 11 through 15, the diameter of the wobble piston is generally about 1.8 inches. The diameter of the second piston head can be approximately 0.875 inches, whereas the diameter of the third piston head is approximately 0.25 inches. The second and third pistons can have a stroke of approximately 1.25 inches, whereas the wobble piston can have a stroke of approximately 0.375 inch. The embodiment of FIG. 11 through 15 also contain check valves, generally before and after each cylinder, to prevent the oxygen enriched gas from being pushed backwards into the preceding cylinder or into the product or buffer tank.

An advantage of the compressor of FIGS. 11–15 is that it generally is compact and small, approximately ⅓ the size of the embodiment of the compressor shown in FIG. 8, and also approximately ⅓ the weigh thereof, so that it can weight only about 40 pounds. Due to the compactness of the alternative compressor, it can be mounted directly or on top of the oxygen concentrator or it can be made an integral part thereof.

Bottle cylinder or high pressure storage container 820, can generally be of any size and contain any pressure although the above noted pressure of approximately 2,000 PSI is desirable. A small bottle of approximately 62 cubic inches can last a patient for approximately two hours. This time can be extended to approximately six hours when utilized in conjunction with a conserving device. A large tank of approximately 283 cubic inches can generally last a patient for approximately eight hours or approximately twenty-four hours when utilized with a conserving device.

Manifold block 810 is located between third piston assembly 770 and bottle 820. The manifold block contains pressure gauge 812 and a high pressure switch which, as explained herein below, turns off the compressor once a predetermined pressure is achieved. The manifold also contains a ruptured disc, not shown, as a safety backup should the pressure to the bottle become too high. The manifold block also contains a bleed-off valve, not shown, which gradually releases the pressure built up in compressor assembly 700 as well as line 789 so that a loud abrupt pressure release noise is not caused. Bottle 820 also contains a ruptured disc thereon, not shown, which is set to rupture at a pressure higher than that of the manifold rupture disc. The bottle can also contain a pressure gauge 822.

The compact compressor 700 can be utilized in the same manner as before, that is in association with an oxygenator and with various flow schemes, designs, etc., whether prioritized to insure that a patient receives a required amount of the oxygen enriched gas, or not prioritized. Accordingly, the flow diagrams of FIGS. 2, 3 or 4, can be utilized but it is to be understood that generally any other flow system can also be utilized to route the enriched oxygen from product tank 30 either directly, or indirectly, etc., to the buffer tank and to compact compressor 700.

Figure 15:
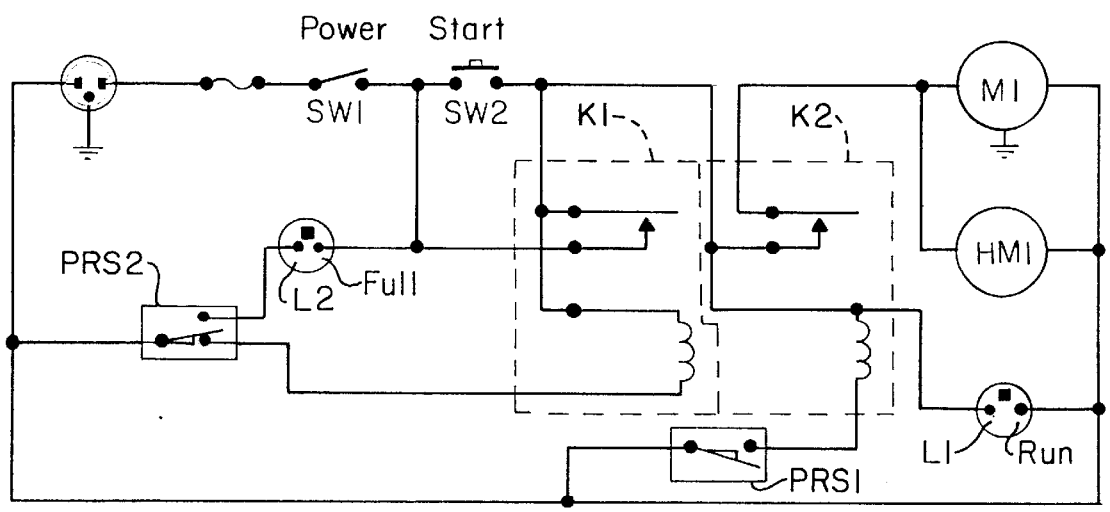

An example of electrical circuitry which can be utilized to operate compact compressor assembly 700 is shown in FIG. 15.

Mains power (line voltage) is supplied through a three conductor grounded line cord. The hot side of the mains power is connected to a resettable thermal circuit breaker. The output lead of the circuit breaker feeds the mains power on/off switch. The neutral side of the mains power is supplied to one side of the High Pressure switch PRS2, Low Pressure switch PRS1, the "Run" light L1, hour meter HM1, and the compressor motor M1.

With the power switch SW1 on, mains hot is supplied to one side of the "Full" light 12, the "Start" switch SW2, and the maintaining contact of relay K1. When the momentary contact "Start" switch SW2 is depressed, power is supplied to the relay K1 coil, one side of the "Run" light L1, the coil of motor relay K2 and the maintaining contact of the motor relay K2. The High Pressure switch PRS2 supplies the neutral mains return to the relay K1 coil if the cylinder pressure is below the full pressure setpoint, latching relay K1 on.

If the Low Pressure switch PRS1 is activated by sensing pressure above its setpoint, K2 is energized, supplying power to the hour meter and the compressor motor. The motor relay will cycle on and off by the low pressure switch if the inlet pressure goes above or below the switch setpoint.

If the cylinder reaches the High Pressure switch PRS2 setpoint, PRS2 will activate, removing neutral power from the coil of latching relay K1 and lighting the "Full" light L2. This will remove power from the K1 coil, causing the latching and motor relays K1 and K2 to be de-energized, stopping the compressor motor and turning off the "Run" light L1.

While in accordance with the patent statutes the best mode and preferred embodiment have been set forth, the scope of the invention is not limited thereto, but rather by the scope of the attached claims.

What is claimed is:

1. An apparatus for compressing and storing an oxygen-enriched gas, comprising;
    an oxygen concentrator product tank having enriched oxygen therein,
    a motor driven compressor operatively connected to said oxygen concentrator product tank to receive oxygen-enriched gas therefrom, said motor driven compressor operated independently of an oxygen concentrator power source and operated by a power source other than oxygen-enriched gas from said concentrator product tank, said motor driven compressor being capable of compressing said oxygen-enriched gas to a high pressure, said motor driven compressor containing a plurality of pistons, wherein a first piston is driven by a first drive shaft and a second piston is driven by a second drive shaft, and a high-pressure storage container operatively connected to said motor driven compressor for portable storage of said high-pressure oxygen-enriched gas, wherein said first piston is a wobble piston and wherein said second piston is a non-wobble piston, wherein said wobble piston compresses said gas from a first pressure to a second pressure and wherein said non-wobble piston compresses said gas from said second pressure to a third pressure.

2. An apparatus for compressing and storing an oxygen-enriched gas according to claim 1, including a second non-wobble piston connected to said second drive shaft, wherein a piston head of said first non-wobble piston has an area which is smaller than a head area of said wobble piston, and wherein a head area of said second non-wobble piston is smaller than the area of said first non-wobble piston head.

3. An apparatus for compressing and storing an oxygen-enriched gas according to claim 2, wherein said first and second non-wobble pistons are substantially longitudinally aligned.

4. An apparatus for compressing and storing an oxygen-enriched gas according to claim 2, including a bleed-off valve located before said high-pressure storage container.

5. An apparatus for compressing and storing an oxygen-enriched gas according to claim 2, including a buffer tank, said buffer tank operatively connected to said oxygen concentrator product tank and to said motor driven compressor, wherein said oxygen-enriched gas is prioritized by primarily being capable of being fed to a person and secondarily any excess oxygen-enriched gas being capable of being fed to said buffer tank, said prioritization including a determination of an oxygen concentration of said gas by an oxygen sensor and a termination of said oxygen-enriched gas being fed to said buffer tank when said oxygen concentration is below a predetermined level.

6. An apparatus for compressing and storing an oxygen-enriched gas according to claim 5, wherein said first and second non-wobble pistons are substantially longitudinally aligned, and wherein said second drive shaft rotates at a slower rate than said first drive shaft.

7. An apparatus for compressing and storing an oxygen-enriched gas according to claim 1, including a buffer tank, said buffer tank operatively connected to said oxygen concentrator product tank and to said motor driven compressor, wherein said oxygen-enriched gas is prioritized by primarily being capable of being fed to a person and secondarily any excess oxygen-enriched gas being capable of being fed to said buffer tank, said prioritization including a determination of an oxygen concentration of said gas by an oxygen sensor and a termination of said oxygen-enriched gas being fed to said buffer tank when said oxygen concentration is below a predetermined level.

8. An apparatus for collecting and storing or distributing an oxygen-enriched gas, comprising;

an oxygen concentration device having an inlet which receives low pressure air and an outlet which provides a source of oxygen-enriched gas at a relatively low pressure to an inlet of a first storage vessel;

a pressure control device which receives a first component of said low pressure oxygen-enriched gas and outputs said oxygen-enriched gas at a reduced predetermined pressure for use by a patient;

a buffer tank having an outlet and an inlet adapted to receive a second component of said oxygen-enriched gas at said low pressure from said first storage vessel outlet;

a second storage vessel having an inlet and an outlet;

a motor driven compressor connected to said buffer tank outlet which compresses said oxygen-enriched gas and outputs oxygen-enriched gas at a relatively high pressure to said inlet of said second storage vessel, wherein said compressor contains at least one wobble piston for compressing said oxygen-enriched gas wherein said motor driven compressor is operated independently of a power source of said oxygen concentration device; and prioritizing apparatus connected between an outlet of said first storage vessel and said motor driven compressor and which interrupts the flow of said second component of oxygen-enriched gas to said motor driven compressor when the pressure of said second component of oxygen-enriched gas falls below a preset amount to ensure that said first component is sufficient to ensure the output of said oxygen-enriched gas from said pressure control device at said reduced predetermined pressure.

9. An apparatus according to claim 8, including said motor driven compressor having a plurality of pistons, including at least one wobble piston for compressing said oxygen-enriched gas to a first pressure, and at least one non-wobble piston for compressing said oxygen enriched gas from said first pressure to a second pressure.

10. An apparatus according to claim 9, wherein said wobble piston is connected to a first drive shaft and wherein said at least one non-wobble piston is connected to a second drive shaft.

11. An apparatus according to claim 10, including at least a second non-wobble piston for compressing said gas from said second pressure to a third pressure, and wherein said second non-wobble piston is connected to said second drive shaft.

12. An apparatus according to claim 11, wherein said first and second non-wobble pistons are substantially longitudinally aligned and wherein said second drive shaft rotates at a slower rate than said first drive shaft.

13. An apparatus according to claim 12, wherein a piston head of said first non-wobble piston has an area which is smaller than a head area of said wobble piston, and wherein a head area of said second non-wobble piston is smaller than the area of said first non-wobble piston head.

14. An apparatus according to claim 12, further comprising a valve element connected between the outlet of said first storage vessel and said motor driven compressor, and an oxygen concentration detector operatively connected to said valve element which monitors said first component of said low pressure oxygen-enriched gas and which operates said valve element to interrupt a flow of said second component of oxygen-enriched gas to said motor driven compressor when a concentration of said second component of oxygen-enriched gas reaches a set limit.

15. A method of providing a portable source of oxygen utilizing a home health care oxygen concentrator having a patient flow line to deliver product gas from a product tank to a patient comprising the steps of:

setting a minimum concentration of oxygen for the product gas and measuring the oxygen concentration of the product gas to establish that the minimum is met;

setting a minimum delivery flow rate of said product gas to said patient; measuring the delivery flow rate to said patient, and if the minimum delivery flow rate and the minimum concentration are met, directing excess product gas to a compressor to compress said product gas, said compressor having at least a first compression stage and a second compression stage wherein one of said first and second compression stages utilizes a wobble piston for compressing said product gas and the other utilizes non-wobble piston for compressing said product gas, and delivering said compressed product gas to a portable storage unit.

16. A method according to claim 15, wherein an excess product gas is directed to said compressor only so long as both the minimum delivery flow rate and the minimum concentration of oxygen in the product gas are met.

17. A method according to claim 16, wherein said first compression stage precedes said second compression stage and utilizes said wobble piston.

18. A method according to claim 17, wherein said second compression stage utilizes multiple non-wobble pistons.

19. A method as set forth in claim 15, wherein the buffer tank contains product gas at a pressure of from about 7 to about 14 psi and the portable storage unit includes compressed product gas at a pressure of from about 500 to about 3,000 psi.

20. A method as set forth in claim 19, wherein said first stage compresses said product gas to a pressure of from about 10 to about 60 psi.

21. A method as set forth in claim 15, wherein said delivery flow rate is from about 0.1 to 6 liters per minute.

22. A method as set forth in claim 15, wherein said wobble piston is connected to a first drive shaft and said non-wobble piston is connected to a second drive shaft.

* * * * *